United States Patent [19]

Osborn et al.

[11] 4,079,312

[45] Mar. 14, 1978

[54] CONTINUOUS TESTING METHOD AND APPARATUS FOR DETERMINING THE MAGNETIC CHARACTERISTICS OF A STRIP OF MOVING MATERIAL, INCLUDING FLUX INDUCING AND PICK-UP DEVICE THEREFOR

[75] Inventors: Merlin L. Osborn, Saxonburg; Layton D. Crytzer, Natrona Heights, both of Pa.

[73] Assignee: Allegheny Ludlum Industries, Inc., Pittsburgh, Pa.

[21] Appl. No.: 715,098

[22] Filed: Aug. 17, 1976

[51] Int. Cl.² ............................................. G01R 33/12
[52] U.S. Cl. ..................................... 324/226; 336/224; 324/225; 324/242; 29/564.3; 29/526.4
[58] Field of Search .................. 324/34 R, 34 PE, 37; 336/130, 170, 173, 222, 224

[56] References Cited

U.S. PATENT DOCUMENTS

| | | | |
|---|---|---|---|
| 2,102,451 | 12/1937 | Zuschlag | 324/37 |
| 2,555,853 | 6/1951 | Irwin | 324/34 R |
| 2,810,880 | 10/1957 | Buccicone | 324/34 R |
| 2,927,266 | 3/1960 | Richter | 324/34 R |

FOREIGN PATENT DOCUMENTS 403,409 12/1933 United Kingdom .............. 324/34 R

Primary Examiner—Robert J. Corcoran
Attorney, Agent, or Firm—Vincent G. Gioia; Robert F. Dropkin

[57] ABSTRACT

Continuous testing apparatus for determining the magnetic characteristics of a strip of moving material including a flux inducing and pick-up device to induce a quantity of flux into the material and dual voltage output producing coils for producing different voltages from material having the same magnetic permeability, and circuit means coupled with the dual coils to produce an output voltage which is a characteristic of the ratio of the voltage produced by one of the coils and the difference between the voltages produced by both of the coils. The invention also includes the method of obtaining a profile of the coil of the material throughout the entire length thereof.

23 Claims, 7 Drawing Figures

CONTINUOUS TESTING METHOD AND APPARATUS FOR DETERMINING THE MAGNETIC CHARACTERISTICS OF A STRIP OF MOVING MATERIAL, INCLUDING FLUX INDUCING AND PICK-UP DEVICE THEREFOR

BACKGROUND OF THE INVENTION

1. Field of the Invention

This invention relates to the continuous testing of strip material for determining the magnetic characteristics thereof.

More particularly, the invention is concerned with apparatus which uses a non-contacting coil arrangement and associated electronic circuitry to monitor the relative magnetic quality of a moving strip of material with no line restrictions or interference. The invention is also concerned with a method for obtaining a profile indicating quality of a coil of strip material throughout the length thereof.

When a change takes place in magnetic properties, this usually indicates that a change has occurred in one of the other variables, such as steel chemistry, mechanical hardness, gauge, grain size or structure, stress relief of work-hardened strip, uniformity and degree of annealing, the presence of faults or occlusions or the like. Such changes are not observable by eye and are generally difficult to detect. A large quantity of defective steel strip may be produced, or stated another way, the steel strip which is produced may not be of uniform quality throughout, and while it may be suitable for one purpose, it may not be suitable for its primary purpose.

It has also been observed that flux will travel further from the source in a good quality strip than in one of poorer quality.

2. Description of the Prior Art

Numerous systems have been developed over the years and several systems are in current use, both in the United States and elsewhere. Most of these use an open solenoid, a single, or a double yoke approach. The magnetizing force is indicated by means of an "H" indicating device such as Chattock coil, Hall probe or exciting current. Induction in the strip is indicated by voltage produced in a coil encircling the strip. Electronics are employed to indicate core loss, permeability or a number correlated to magnetic quality.

For example, U.S. Pat. No. 3,130,363 is concerned with apparatus for determining the magnetic condition of a moving strip, and in particular, the magnetic condition of steel strip being continuously annealed in order to adjust for proper annealing temperature. In particular, use is made of a detector head mounted in a tube which is placed into a heating chamber of a furnace to ascertain whether the temperature of the strip is above or below the Curie point. The detector head used is a single H-shaped core having identical coils wound on the legs. Operation is based on ascertaining when the system is below the Curie point, and at that time the detector head indicates an imbalance. When balanced, there is no conductivity.

U.S. Pat. No. 3,281,678 is also concerned with determining the magnetic properties of strip material. It is known that the quality of sheet or strip steel is dependent upon its magnetic properties. For this purpose, this patent is directed to a magnetic core loss tester and uses only two coils. One is a "B" coil and the other is an "H" coil which provides an indication of core loss in watts per pound. A ratio meter is also used to obtain magnetic permeability or $\mu$ and this reads the ratio of B/H directly. Accordingly, only two coils are used which surround the strip steel, the magnetizing coil B and the sensing coil H. In effect, this patent discloses sophisticated circuitry for obtaining core loss and permeability.

U.S. Pat. No. 3,421,925 is also concerned with the improvement of the final product of strip steel as well as to avoid relatively poor electrical performance of strip steel. For this purpose, this patent proposes method and apparatus to continuously test the strip for core loss or watts loss per pound as it is being processed. The test apparatus includes a conventional "M" coil for applying a magnetizing force of predetermined magnitude, a "B" coil for measuring the total flux in the strip and the surrounding air, and an "H" coil for measuring the flux in the surrounding air only. This patent must use the thickness of the steel as one of its variables, and for this purpose, it employs an X-ray gauge to determine the thickness of the steel, and the signal from the "B" and the "H" coils are coupled with the signals from the X-ray gauge to produce a continuous record of watts loss per pound of the material, and thereby provide a record of the electrical quality of the steel.

U.S. Pat. No. 3,444,458 is also concerned with the detection of variations in the magnetic properties of steel, and more particularly, for detecting variations in the quality of continuous steel strip moving in a processing line. This patent discloses a detecting device which includes a pair of matched cores for placement on opposite sides of a strip of ferromagnetic material with their ends in opposition and provided with a space or air gap through which a strip to be tested is passed. The cores are energized and by passing the strip material through the air gap, the reluctance of the circuit is changed. When there is a change in the output voltage, this indicates a change in the characteristics of the strip. Use is made of two windings on a single core, but one winding is used as a reference winding to obtain a zero or null position on an output meter and the other winding is used as an excitation winding.

Siemens German Pat. No. 1,120,591 is also concerned with the measurement of the magnetic properties of electrical sheet strip which may be of non-uniform cross-section. When the cross-section is not uniform, then, as is well-known, variations due to magnetic inductions occur so that the measurements taken are not exact. This patent proposes the use of rollers positioned at the yoke ends which can be raised to provide a voltage proportional to the thickness of the material which passes under the rollers. A number of coils are arranged in parallel, but are aligned in a tandem relationship as the strip passes through the coils so that only the strip is magnetically energized. Since the rollers are vertically movable, correction of the magnetic values in accordance with thickness is obtained.

U.S. Pat. No. 3,748,575 is also concerned with the testing of the characteristics of a moving metal strip. A magnetic monitoring device is located within a hollow member so that any irregularities in the advancing strip do not affect the monitoring device. The magnetic characteristic of the strip is monitored by using a first magnetic head to record a magnetic signal onto the strip and then a second magnetic head displaced from the first magnetic head is used to sense the signal so recorded as the strip passes the second magnetic head. The two magnetic heads are required to be maintained at a fixed separation and are angularly spaced from each other by a fixed predetermined angle. A magnetic screen is also interposed between the two magnetic heads to prevent interaction therebetween. Regular, but intermittent and non-continuous readings of the magnetic characteristics are obtained.

British Pat. No. 928,500 is also concerned with method and apparatus for the measurement of magnetic properties, such as core loss and permeability of a moving strip of steel. A magnetic yoke is brought into contact intermittently with a traveling steel strip which yoke has an excitation and an induction winding. Current is induced into the strip and the induced current is measured to provide an induction of the magnetic, and electrical, properties of the steel.

U.S. Pat. No. 3,723,859 is also concerned with the testing of the characteristics of a moving metal strip and in particular with the monitoring and recording of steel characteristics in a continuously moving strip of steel. However, in this system, thickness is one quantity which is determined as well as permeability and loss of a moving strip of electrical core steel. Measurements are taken at different positions. In the system according to this patent, apparatus is provided to establish the same flux density at two different positions of the moving strip of steel.

At present, standard magnetic quality tests are conducted by removing a test panel or panels from ends of a coil. The coil is graded by core loss using these tests. If a coil end is of poor quality, it is a general practice to remove a portion of the material and to retest. The "cutback" procedure is an estimate based on experience and can be a waste of time, manpower and equipment and may result in scrapping salable material. The standard tests provide only a test of the material where the panel is removed and do not indicate magnetic quality throughout the coil. Commercial test units have been developed which are very expensive ($200,000 to $500,000) but strip width, gauge and quality variations complicate the electronics and, in general, the units may have variations in test level accuracy that are caused by changes in the quality level of the material under test.

SUMMARY OF THE INVENTION

In order to take advantage of our appreciation, during studies of various means to monitor electrical strip continuously, that flux will travel further from the source in a good quality strip than one in a poorer quality, we have proposed to use this principle to provide for a non-contacting coil arrangement and associated electronics to monitor relative magnetic quality of a moving strip with little line restrictions.

In general, the invention is usable to eliminate material with undesired characteristics, such as for "cutback" procedures and as a test device to determine relative magnetic quality throughout a coil of material. When used as a test device, it is usable for process control and evaluation purposes during new material trials or process changes.

Accordingly, it is an object of the present invention to provide a device to indicate relative "down strip" quality.

A further object of the invention is to provide a method of obtaining a profile indicating quality of a coil of steel strip material throughout the entire length thereof.

Yet another object of the invention is to provide for a simple, inexpensive device with little maintenance and line restriction problems.

The invention is usable almost anywhere along the line of travel of the steel strip. For example, it is possible to use it at the slitter line, the scrub line, heat flatening line, or anywhere after the high temperature anneal.

An important aspect of the invention is that it is possible to obtain a recorded profile of the strip of material while it is being manufactured. This profile may be used to demonstrate the characteristic of the steel along its length. Where the profile shows an indication of quality different from that which is desired, the portion of undesired quality may be cut out and removed from the roll. Furthermore, since a permanent record of the steel quality and characteristic is obtainable, no wastage occurs as steel strips of similar quality and characteristics may be combined to provide for usable rather than wasted material.

The invention is just as well usable with old material as with new.

Moreover, it is possible to stop the steep strip processing operation when the strip quality falls below a predetermined level and thereby avoid long pieces of strip material of undesired quality and characteristics.

The invention is usable as a quality control device, a continuous test apparatus and method, a magnetic profile determiner, as well as a static tester. In general, strip width and gauge changes can for all practical purposes be ignored. Static tests and line trials at speeds of 100 to 600 feet per minute give the desired results without complicated electronic circuitry.

The apparatus according to the invention generally consists of three basic sections. One is an excitation and pick-up coil section; a second is a signal processing electronics section; and the third is a readout section including the provision of the preparation of directly readable and calibratable charts.

More specifically, the invention is concerned with a continuous testing apparatus for determining the magnetic characteristics of a strip of moving material which includes a flux inducing and pick-up device having means to induce a flux into the strip of moving material to produce a magnetizing force and means to pick-up two quantities characteristic of the same flux induced to produce a voltage output for each of the quantities with the voltage outputs differing from each other, and means responsive to the voltage outputs to produce a third output voltage which is a ratio of the output voltage of one of the quantities divided by the difference between the first voltage output and the other of the aforesaid output voltages so that the overall average ratio is indicative of overall quality of the material.

The flux inducing and pick-up device according to the invention is adapted for the measurement of flux induced into the strip of moving steel which has a substantially uniform width and thickness and includes a magnetization coil for inducing the magnetic flux into the strip of moving steel, and two flux pick-up coils, the first flux pick-up coil is associated with the magnetization coil and is responsive to the flux induced into the strip of moving steel, and has a first characteristic for producing an output in accordance with its characteristic and the flux induced into the steel by the magnetization coil, and the second flux pick-up coils is associated both with the first coil and the magnetization coil and is responsive to the flux induced into the strip of moving steel, but the second coil has a second characteristic which is different from the characteristic of the first coil so as to produce an output in accordance with the second characteristic and the flux induced into the steel by the magnetization coil, and thereby produce a second output which is different from the first output.

The apparatus according to the invention also provides that the first pick-up coil will produce a voltage greater than the voltage of the second pick-up coil, and as part of the responsive means, there are provided two circuits, one for each pick-up coil, one circuit is coupled with the first pick-up coil and includes means to produce a rectified voltage whose magnitude is characteristic of the voltage induced in the first pick-up coil, nd the second circuit is coupled with both of the pick-up coils to produced a rectified voltage whose magnitude is characteristic of the voltage induced in both of the pick-up coils, and in particular a voltage which is proportional to the difference between the voltages from each of the pick-up coils, and divider means is provided, coupled to both of the circuits to produce an output voltage derived from dividing the voltage output from the first circuit by the voltage output from the second circuit.

The invention is also useful to obtain a profile indicating quality of a coil of steel strip material throughout the entire length thereof, wherein the coil can be cut to remove sections of material which deviate from a predetermined set standard, the profile being obtained by magnetizing a continuous strip of moving material to a predetermined level of magnetization, then taking a first voltage reading indicative of the magnetization induced into said moving strip of material, taking a second voltage reading indicative of the magnetization induced into said strip of moving material, the first and second readings being preferably taken over substantially the same portion of the strip of material. Such readings may be taken over different portions of the strip material. As a matter of electrical convenience, the second reading is designed such that it does not exceed 90% of the first reading, and then a ratio between the first reading and the difference between the first and the second readings is obtained whereby to provide a continuous reading indicative of the ratio for all positions of the strip. Such readings may also be plotted to provide a graphical representation of the coil of strip material.

The invention is also concerned with a method of testing steel strip material, which comprises the steps of applying a predetermined quantity of magnetizing flux to a predetermined area of the steel strip material as it is moved past a flux application position, obtaining a first measurement of the flux applied to the predetermined area, then obtaining a second measurement of the flux applied to the predetermined area as a predetermined percentage of the first obtained measurement, combining said first and second obtained measurements to obtain the difference therebetween to obtain a third measurement characteristic of said combined measurements, and then comparing one of the first and second measurements with the third measurement to obtain a ratio between the first or second measurement to the third measurement.

The second measurement of the flux applied to the predetermined area is selected at a maximum of 90% of the first obtained measurement as a matter of electrical convenience. The device will operate and the method can be carried out at different percentages.

BRIEF DESCRIPTION OF THE DRAWINGS

Other objects, advantages and the nature of the invention will be more fully understood from the following description of the preferred embodiment of the invention, shown, by way of example, in the accompanying drawings.

DESCRIPTION OF THE PREFERRED EMBODIMENTS

Figure 1:
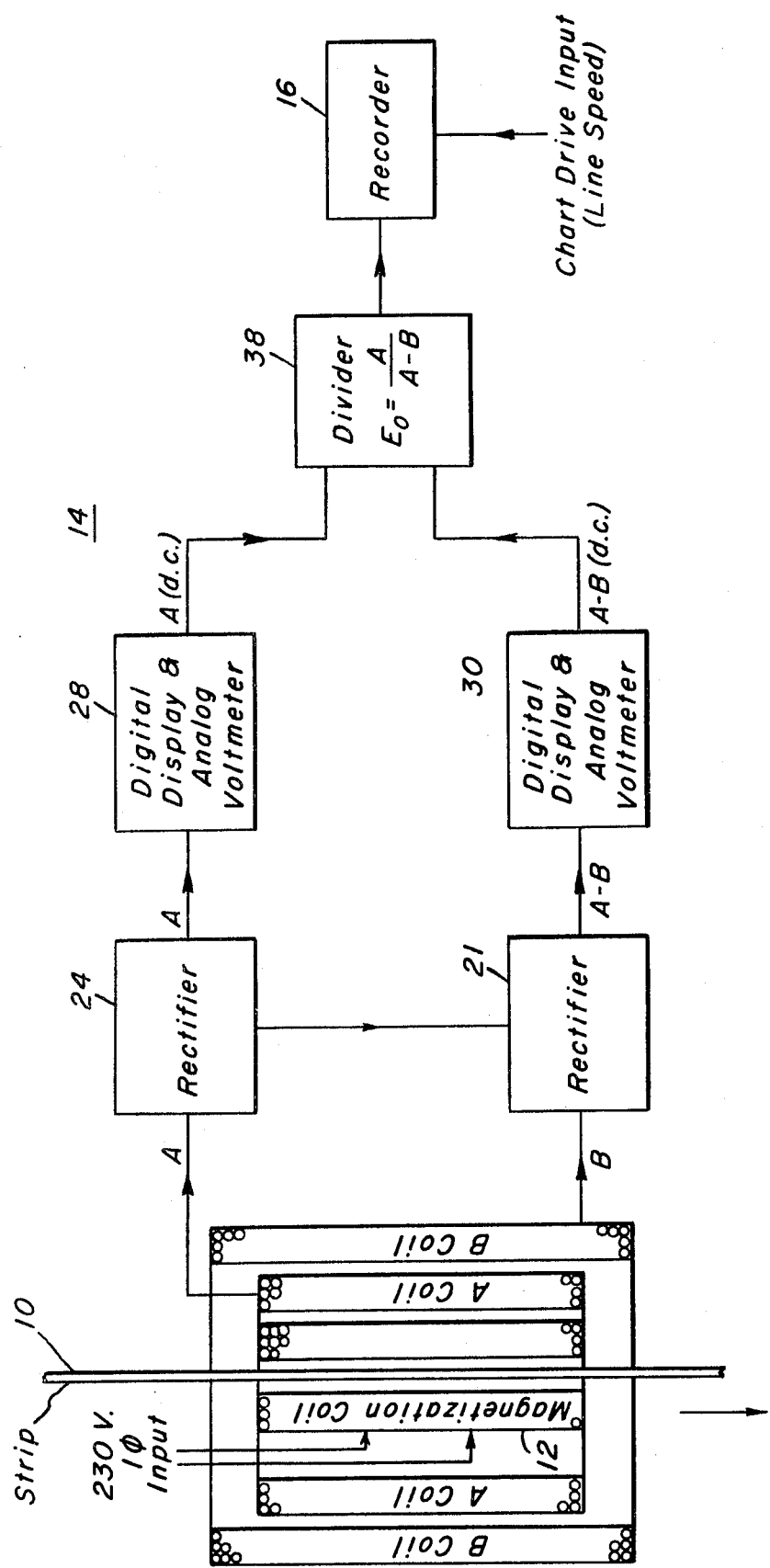
FIG. 1 is a block diagram is schematic form of the continuous testing apparatus according to the invention.

Referring to the drawings which show the preferred apparatus for carrying out the invention, FIG. 1 shows a strip of material 10 which forms part of a large coil of strip material, only a portion of which is illustrated, being moved past a flux inducing and pick-up device which is generally comprised of magnetization coil 12 and pick-up coils A and B. FIG. 1 shows the magnetizing coil 12 and pick up coils A and B in schematic form, and reference is made to FIGS. 3 and 4 to show their constructional configuration and spacial relationship. The outputs of coils A and B are coupled to ratio producing voltage output circuit 14 and a continuous recorder 16.

Figure 2:
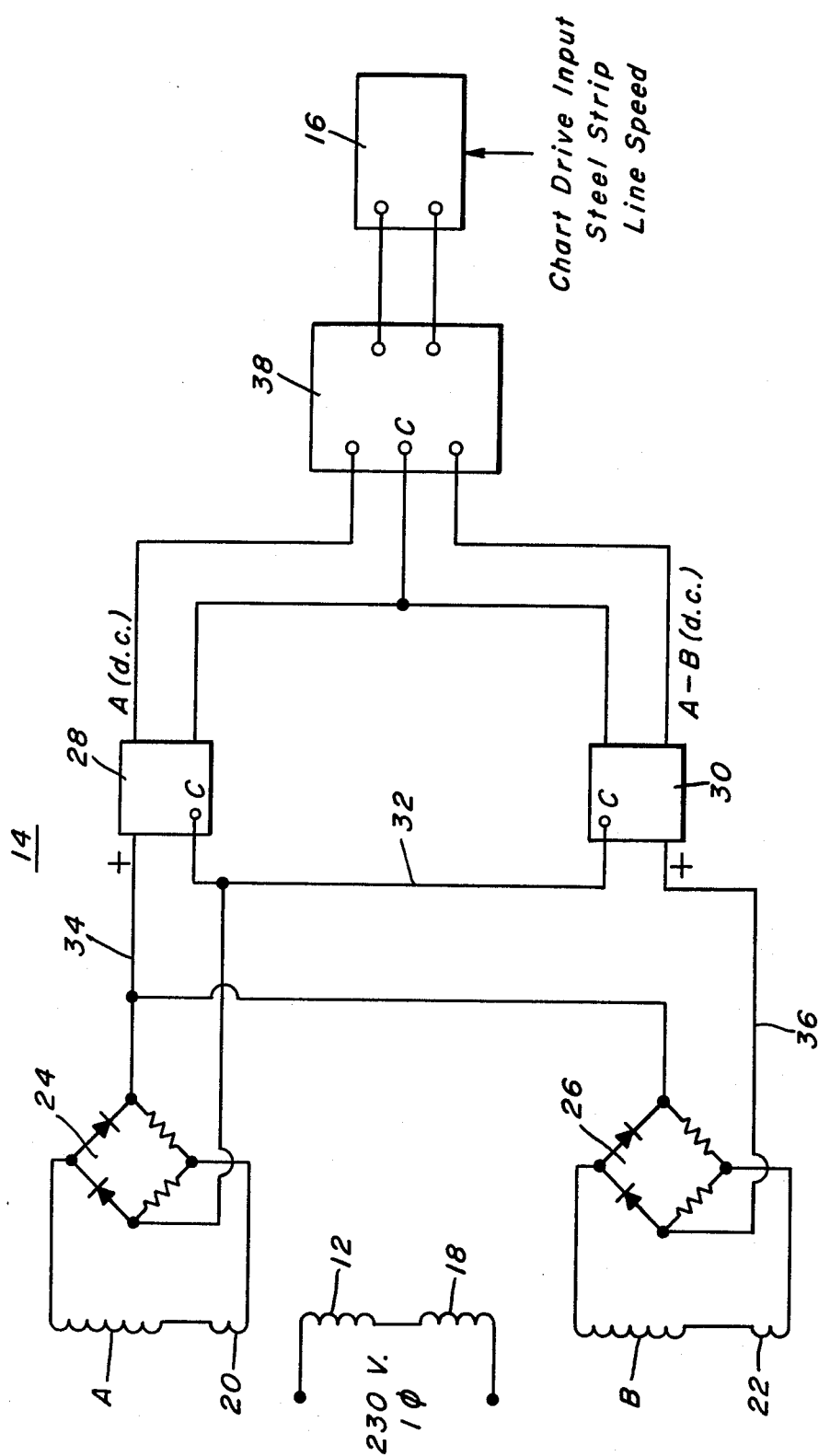
FIG. 2 is a circuit diagram of the block diagram of FIG. 1.

Referring now more particularly to FIGS. 1 and 2, magnetization coil 12 to magnetize strip material 10 is connected across, for example, a single phase 230 volt, 60 Hertz supply and in circuit with primary coil 18 for air compensation as part of the means to eliminate air pick-up in the coil system. Voltage adjustment is made with a variable control or a current control of the conventional type in circuit with magnetization coil 12, not shown, in order to adjust the magnetization current in the magnetization coil so that it will magentize strip material 10 at or near the 10H (10 oersted) level. While a particular power source has been shown for purposes of explanation, it is to be understood that it is within the scope of the invention to use a 110 volt supply or any other suitable convenient power supply. Induction level in strip material 10 is not critical, but experience has shown that if the strip material is magnetized to or near the 10H (10 oersted) level when the Epstein test result at 10 oersteds is used as the quality indication, then a better correlation is achieved. The current level can change slightly as the strip 10 moves through the apparatus or test device without detrimental effect. As is well known, with any given strip quality, the current in the excitation or magnetization coil 12 is proportional to the magnetizing force. This means that if the current level changes, the magnetizing force (10 oersteds) would change. This change is not critical, but in order to avoid a large change, a constant current source should be used.

Coils A and B are also connected with secondary compensating coils 20 and 22, respectively, which together with primary coil 18 form the air compensation system, and the voltage outputs from coils A and B are connected across full wave diode bridges or rectifiers 24 and 26, respectively. The rectified output voltage from rectifier 24 is desirably fed to an analog meter to obtain an analog of the voltage A (D.C.) obtained from coil A, and as an example a digital D.C. Voltmeter 28 may be used to provide such analog of the voltage A (D.C.) obtained from coil A. The voltage from coil B and the rectified voltage of coil A from rectifier 24 are fed to rectifier 26 in phase relationship to obtain a rectified voltage output from rectifier 26 which is a difference voltage between the voltages of coils A and B. The rectified difference voltage of coils A and B is fed to another analog meter, such as, for example, a digital D.C. voltmeter 30 to obtain an analog output A - B (D.C.) therefrom which is indicative of the difference between the voltages obtained from coils A and B. As will be explained subsequently, coils A and B are so related that the voltage output of coil A will always be greater than the voltage output from coil B. Stated another way, coils A and B are so designed that for the same flux quantity induced into strip 10 by magnetization coil 12, coil A will always have a greater voltage output that coil B.

Rectifier 24 is directly connected across coil A to rectify the voltage sensed thereby and to feed the same to digital voltmeter 28 and rectifier 26 is directly connected across coil B to rectify the voltage sensed thereby, and in series opposition with rectifier 24 to feed the difference voltage between coils A and B to digital voltmeter 30. It is also possible to connect rectifier 26 directly across coils A and B, but in phase opposition so that rectifier 26 will rectify and produce an output which is the difference between voltages A and B. Digital voltmeters 28 and 30 may also include a display portion to provide a visual indication of the voltage picked up by coil A, and the difference voltage A — B picked up by coils A and B. Digital voltmeters 28 and 30 have their common or ground connection joined by line 32, and the net magnitude of the voltage from rectifier 24 is fed to digital voltmeter 28 by means of line 34, and the net magnitude of the voltage from rectifier 26 is fed to digital voltmeter 30 by line 36. Coupled to the output of voltmeters 28 and 30 is a divider 38 which is so connected that a ratio of the outputs A/(A — B) is obtained.

Figure 3:
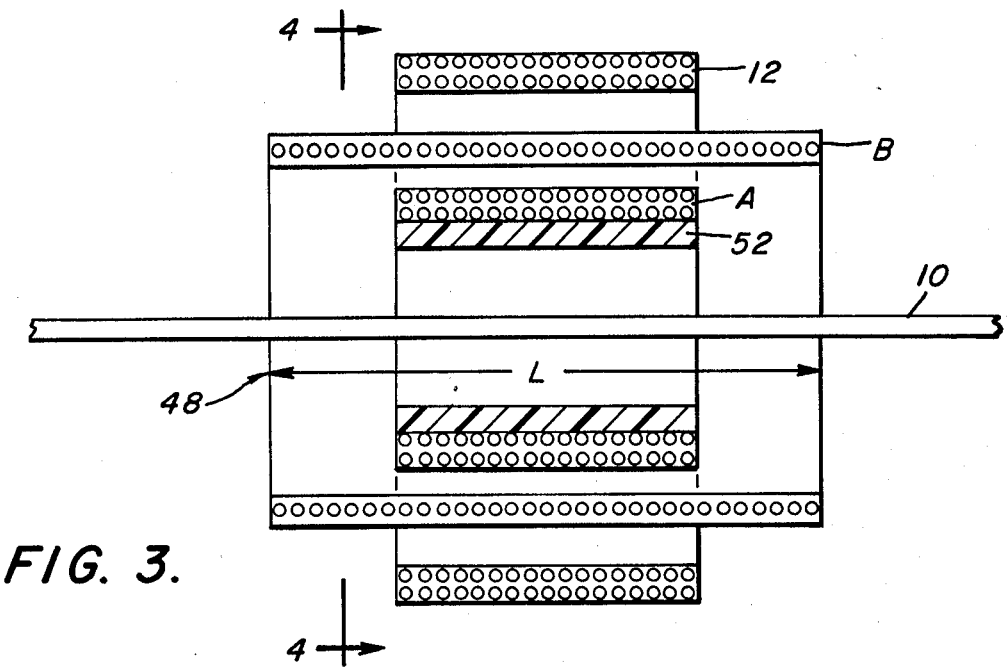
FIG. 3 is a schematic representative of a sectional view taken on line 3–3 of FIG. 4 of a test strip being passed through a magnetization coil and dual pick-up coil arrangement according to one embodiment of the invention.
Figure 4:
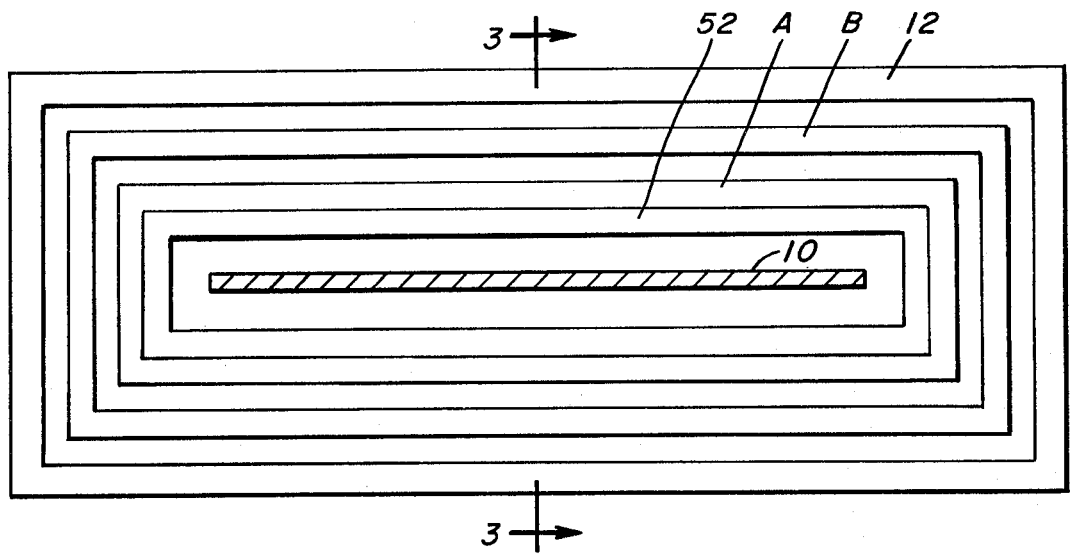
FIG. 4 is a sectional view taken on line 4—4 of FIG. 3.
Figure 5:
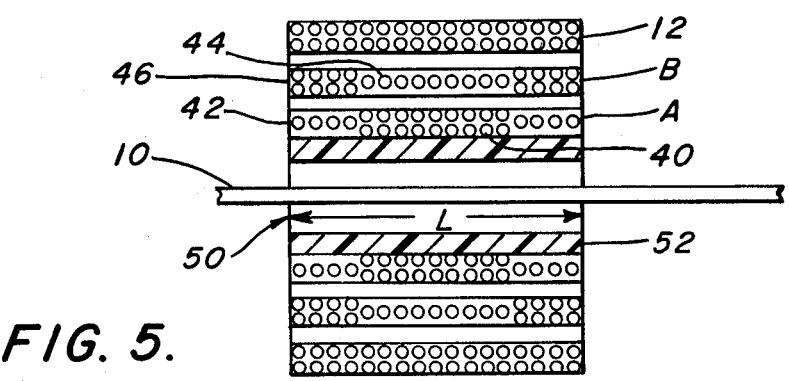
FIG. 5 is a view similar to FIG. 3, but showing another embodiment of the magnetization coil and dual coil pick-up arrangement.

In FIGS. 3 and 4, magnetization coil 12 and pick-up coil A are shown as substantially the same size with pick-up coil B somewhat larger. In FIG. 5, all three coils, the magnetization coil and pick-up coils A and B are shown as the same size. In the embodiment of FIGS. 3 and 4, magnetization coil 12, provides the source of magnetizing force and is wound of insulated heavy copper wire over the two pick-up coils, all three of which are wound on a form which encircle the strip under test. The A coil is composed of a uniformly would coil of sufficient turns to give an adequate voltage pick-up in the operating induction range of the strip and is generally concentrated over the more or less uniform induction range produced by the exciting coil in the strip. The B coil is wound over a longer "down strip" distance than the A coil and thus extends beyond the exciting coil and the A coil into the nonuniform flux area of the strip. The B coil's pick-up voltage is partially obtained from areas where the induction level falls below that of the area beneath the A coil. Changes of B coil length and turns distribution change the shape of the calibration curve of the equipment. Tests have indicated that the B coil should produce a voltage approximately 90% that of the A coil in the highest quality strip for best results so that turns and spacing are adjusted accordingly.

Since, as the strip magnetic quality deteriorates, the B voltage pick-up will drop relatively more than the A coil, because more flux escapes detection by the B coil, the ratio of voltages will indicate strip quality. Since the ratio A/B or B/A is small, it is the practice to determine the solution of the equation A/(A — B) electrically and relate this solution to strip quality as measured by the standard stress-relief annealed Epstein test. Thus, strip condition at the time and condition of test is related to the final evaluation test of coil properties.

Because a ratio of voltages over a relatively short distance of strip is used as the indication of strip quality and the A and B coils obtain their voltages from the same general strip area, strip width and thickness variations, as set forth heretofore, may be ignored.

It should be noted that the two pick-up coils A and B do not have to be any specific length, but for manufacturing purposes, it is desirable for coil A, which is wound on form 52, and magnetization coil 12 to be of the same length. In fact, it may be desirable to make all three coils the same length as shown in FIG. 5's embodiment. What is important is that coil B at its ideal size as mentioned earlier is designed such that it only sees 90% of the voltage that coil A sees, and that the pick-up coils be different. In consequence of this requirement, coil B must always have an effective number of turns which is less than the effective number of turns of coil A so that the B coil will always pick up less voltage than the A coil. Nevertheless, it is also important that the B coil see the same width and thickness of the strip as the A coil in order to eliminate the width and thickness considerations from the testing.

It was indicated in an earlier portion of the specification, that the invention was usable at the slitter line, the scrub line, the heat flattening line, or anywhere after the high temperature anneal, and it should also be noted that while use may be made anywhere, the curve or graphical representation which is obtained as a recorded profile of the strip may require interpretation based on the condition of the strip. Nevertheless, an immediate visual indication related to the steel strip is obtained from the recorded profile thereof as the steel strip is manufactured.

In addition, it is within the scope of the invention to place the B coil "down strip" or at place other than under the A coil so that the readings from the A coil and the B coil may be taken at different portions of the strip material. In this last-mentioned situation, where the B coil is placed "down strip," then additional electronic considerations of width and thickness must be entered into the equipment or the assumption made that the variation does not exist. For this reason, it is important and desirable that the B coil see the same width and thickness of the strip as the A coil in order to eliminate the width and thickness considerations from the testing.

As known from the following formula:

$$E = N \frac{d\phi}{dt} dt$$

where $N$ is the number of coil turns; $d\phi/dt$ is the rate of change of flux with time; $dt$ is the time interval; $E$ is the induced voltage; and for the B coil to have slightly lower induction, it has to be exposed to an area of less average flux density than the A coil so that the B coil will have a lower induced voltage. It is also known that the maximum flux which is induced into strip 10 will generally occur at the center of magnetization coil 12 and that as one moves away from the center less flux due to losses will be induced. If the voltage that coils A and B pick up both get larger then the quality of the steel improves. If the voltage that coil B picks up goes up faster than the voltage that coil A picks up, then the steel quality is better. Therefore, with the following ratio formula:

A/(A − B)

as the ratio goes up, this means that the permeability increases, and the steel quality increases. Stated another way, as the core loss decreases, a better magnetic quality steel is obtained with a higher permeability.

When the embodiment of FIGS. 3 and 4 is used, not only is it important that coil A have more voltage producing turns than coil B, but coil B must have more turns displaced from the center of the combined unit formed of the magnetization coil 12 and coils A and B. The center here referred to is the distance between the axial extent of the combined or composite unit 50 and not the geometric center through which strip 10 passes for testing purposes.

When coils A and B have the same physical size as exemplified in the FIG. 5 embodiment, then the turns of coil A must be greater at the center of the coil than coil B, and for this purpose coil A is shown on Form 52 as having a double layer of turns at 40 and a single layer of turns at 42. Coil B is shown as having a single layer of turns at 44 near the center thereof and a double layer of turns at 46 at the ends thereof to provide a greater density of turns at the ends of the coil rather than at the center. In this manner, while coils B and A are of the same size longitudinally of the axial extent of the composite unit, coil B is exposed to an area of less average flux density than coil A, so that a lower voltage will be induced into coil B than into coil A. Because of the position of the turns, if the steel quality varies in the area and length 48 in FIG. 3 or 50 in FIG. 5 of the coil passing through the composite unit, should there be a variation in the steel quality in length 48 or 50, then the ratio would be less.

Because the voltage from coil A and coil B are determined by the flux change per unit time in the strip material, the voltages induced into these coils are proportional to the induction level in the strip material. With uniform steel quality throughout the length L, coil A would sense, for example, 10 volts and coil B would sense 9 volts to provide the following ratio:

$$\frac{A}{A-B} = \frac{10}{10-9} = 10$$

but, if coil B now only sensed 8 volts because of a decreased coil quality, the ratio would be as follows:

$$\frac{A}{A-B} = \frac{10}{10-8} = \frac{10}{2} = 5$$

and thereby show a considerable drop. These voltages are derived from the analog meters 28 and 30 which in turn are proportional to the inductions produced, or to the voltages as seen by coils A and B. Furthermore, if the maximum amount to which the steel strip 10 could be magnetized was a magnetizing force in strip L which would produce an output voltage of 9 volts, then coil A would only sense 9 volts and coil B would only sense 8.1 volts, assuming uniform coil quality throughout the length L, and the following ratio would be obtained.

$$\frac{A}{A-B} = \frac{9}{9-8.1} = \frac{9}{.9} = 10.$$

But, if the quality in the length L changed, and coil A indicated that strip 10 was being magnetized to a magnetizing force which would produce an output voltage of 10 volts at one point in the length L, and to a magnetizing force which would produce an output voltage of 9 volts at another point in the length L, then the ratio would vary or deviate from the mean average. If coil A were sensing 10 volts and coil B started to sense a lower value than 90% of the 10 volts, the ratio would then deviate from the mean average.

While two embodiments have been shown, one with coil A smaller than coil B in axial extent, and another with coil A and coil B, the same size in axial extent, it is to be noted that coils A and B must pick up different voltages for the same permeability. It is therefore possible to design a pair of pick-up coils A and B in such a manner that coil A has a larger axial extent than coil B, or to design coils A and B in such a manner that coil B is split into two coils and is placed on opposite sides of coil A or to extend beyond the axial extent of coil A. In any event, in such designs, coil B should be designed so that it will only pick up 90% of the voltage which coil A picks up when the magnetic quality of the steel is uniform throughout the portion thereof passing past coils A and B. And, as noted heretofore, both coils A and B should sense the same width and thickness of the steel strip material 10 in order to eliminate strip width and thickness variations entering into the electronics.

Figure 6:
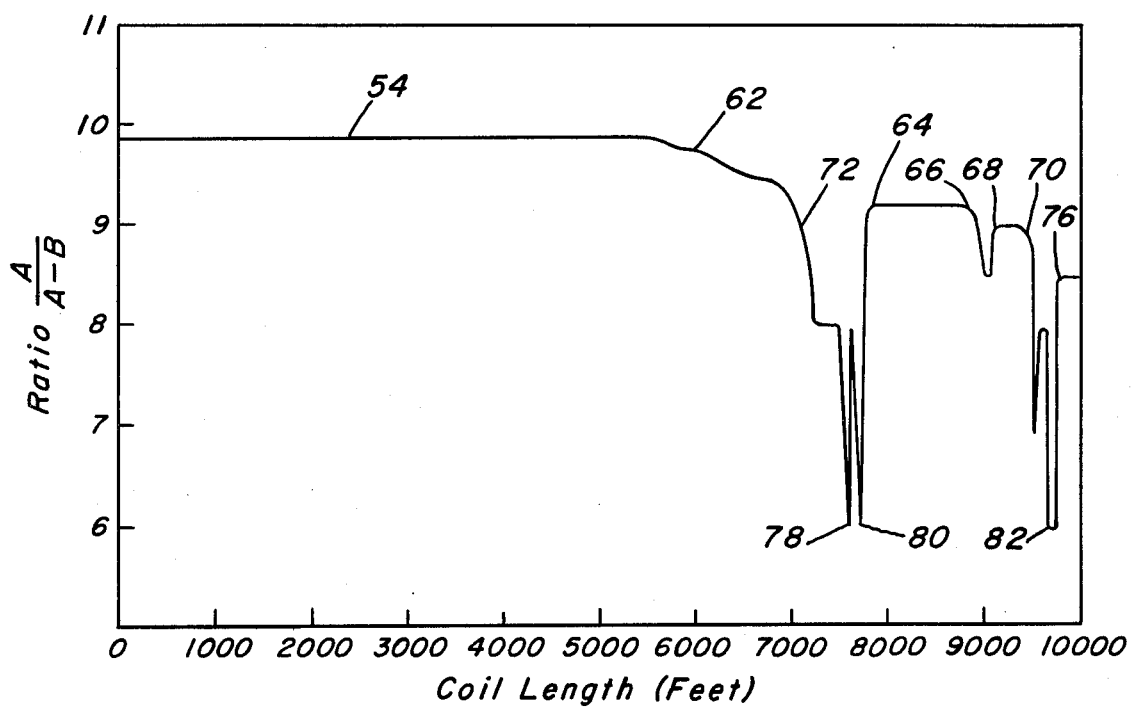
FIG. 6 is a graphical representation of an atypical strip profile of a coil of experimental steel strip material to demonstrate a condition that might be picked up by the continuous testing apparatus of FIG. 1; and, FIG. 7 is a graphical representation of a calibration curve which relates the stress-relief annealed Epstein test to test results obtained according to the invention.

FIG. 6 shows a graphical representation of an atypical strip profile of a coil of strip material. The strip profile was obtained from a coil of experimental material in order to magnify and to accentuate various conditions which the tester according to the invention is adapted to pick up. It will be noted that the ratio of A/(A − B) is plotted as the ordinate and the coil length is plotted as the abscissa. It will be noted that the coil length from 0 feet to about 6,000 feet at point 62 on graph 54 shows substantially uniform overall quality. From point 62 to point 64, the steel strip may be cut out, and the portion from point 64 to 66, might be cut and joined with a piece from point 68 and 70, with the portion between 66 and 68 removed. For certain purposes, the portion between points 62 and 72 might be joined to the portion between 68 and 70 to provide a coil of substantial uniform minimum quality. It will be obvious from the profile as to which portion of the coil was good and which was not.

Figure 7:
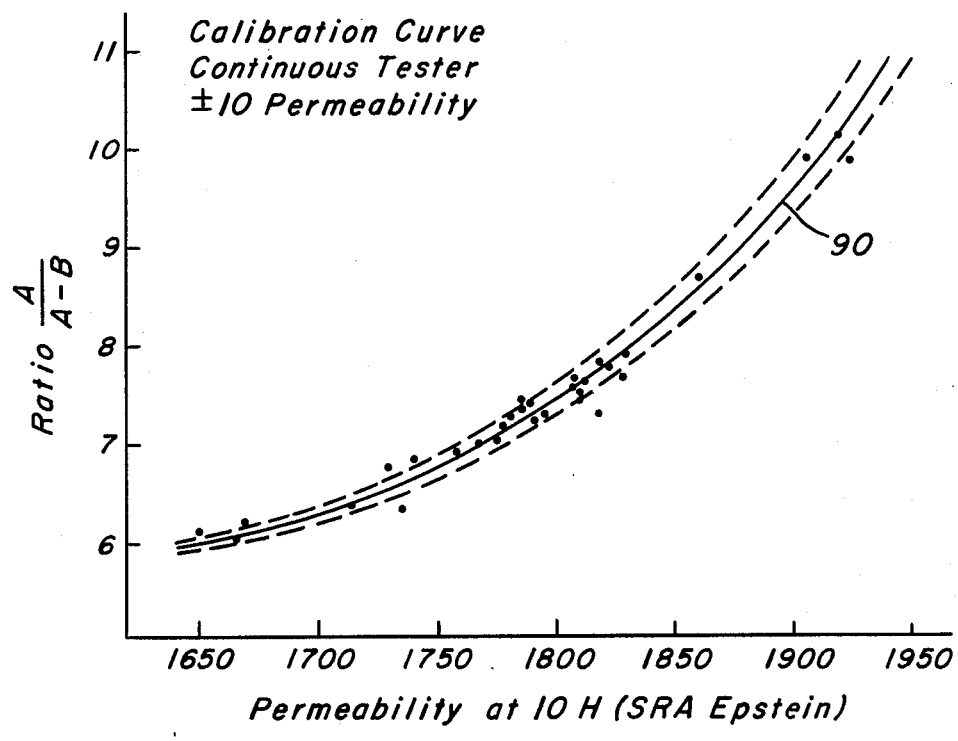

FIG. 7 is a graphical representation of a calibration usable with the continuous tester according to the invention. The abscissa indicates permeability at 10 oersteds so that it can be compared to the stress-relief-annealed Epstein test, and the ordinate indicates the ratio of A/A−B as determined from the circuit according to the invention. As is well-known, the Epstein test measures the total core loss, which is the sum of eddy current and hysteresis current losses. The Epstein test was performed in accordance with the procedure by cutting test panels at specific locations into strips as indicated in ASTMA-343-69. Accordingly, for grain oriented material, a 30.5 cm sample is used which is cut with the rolling direction, and for the non-oriented silicon steel product, a test sample of 28 cm in length and the conventional 3 cm width is cut half parallel to the direction of final rolling and half across the direction of rolling. The data obtained from the cut strips were obtained from the conventional Epstein test method. The data obtained from the continuous test device was obtained from the strip material before the samples were cut by observing the ratio on the strip chart recorder 16. These figures were plotted as ordinate values against abscissa values obtained from the Epstein test in order to obtain curve 90. It will be noted that those portions which indicate a low permeability also indicate a low ratio figure. The coil for which the profile in FIG. 6 is drawn is generally a high grain oriented coil with several poor areas, particularly between 72 and 64, and 70 and 76. Also note low points at 78, 80 and 82 where the ratio is 6. In order to obtain the quality profile of the coil shown in FIG. 6, it was necessary to use experimental material consisting of several poor areas so as to emphasize the ability of using the ratio of A/(A − B) to obtain characteristics related to the Epstein test.

When samples of the coil were taken at different points and subjected to the Epstein test and compared with the ratio A/(A − B) derived according to this invention, the following results were obtained as set forth in Table 1:

Table 1

| Sample | Ratio | SRA Epstein | |
|---|---|---|---|
| | | μ10H | 17kG WPP |
| 1 | 9.0 | 1858 | .763 |
| 2 | 6.30 | 1737 | .992 |
| 3 | 8.25 | 1818 | .837 |
| 4 | 7.25 | 1796 | .862 |
| 5 | 7.00 | 1777 | .888 |
| 6 | 6.00 | 1667 | 1.15 |

Regarding the units used, digital D.C. voltmeter 28 is a 5230 multimeter and D.C. voltmeter 30 is a 5900 multimeter obtainable from Dana Laboratories. Divider 38 is a D-211 Divider obtained from Intronics, Inc. A digital meter model 8375 A for the ratio readout or recorder 16 is obtained from John Fluke Mfg. Co. The rectifiers 24 and 26 are IN-646 Bridge Diodes, and the recorder strip chart is a Model 7100B obtainable from Hewlett Packard. With the aforesaid units, the best mode known to obtain the results herein set forth and practice the invention has been disclosed.

From the above, it should be apparent then that the continuous test device is based on a completely different principle. There is no concern with the nagnetizing force other than putting a certain current through an excitation coil and holding it relatively steady. This means that the material is working above the knee of the B-H curve in most cases, although it can work below, and that the A and B coils are simply an indication of induction in the strip underneath the coil itself. With the assumption that the gauge or width does not change radically in a strip in the length of the span of the B coil, it is possible for all practical purposes to eliminate the width and thickness parameters. It should be pointed out that if the gauge or width does change radically in a very short distance, the device will indicate a change. If one assumes that the change is suddenly under one portion of the B coil and not yet under the A coil, it can be seen that the A − B difference may change resulting in a ratio change if the A coil has not responded to the change of conditions. The overall average ratio should remain indicative of overall quality. This is not likely to occur in a mill situation or if it does occur, the device should return to the original ratio as soon as the width and thickness return to uniform dimensions.

While a specific embodiment of the invention has been shown and described in detail, it will be readily understood and appreciated that various changes or modifications thereof may be made therein without departing from the spirit and scope of the invention as set forth in the appended claims.

What is claimed is:

1. A method of obtaining a profile indicating quality of a coil of steel strip material throughout the entire length thereof, wherein the coil can be cut to remove sections of material which deviate from a predetermined set standard, comprising the steps of:

magnetizing a continuous strip of moving material to a specific level of magnetization, taking a first voltage reading indicative of the magnetization induced into said moving strip of material, taking a second voltage reading indicative of the magnetization induced into said strip of moving material to provide a voltage output different from said first voltage reading;

said first and second readings being taken over substantially the same portion of said strip of material in such a manner that said second reading selectively does not exceed 90% of said first reading, and obtaining a ratio between said first reading and the difference between said first and said second readings whereby to provide a continuous reading indicative of said ratio for all positions of said strip.

2. The method as claimed in claim 1, including the steps of:

subjecting said strip of material to a level of approximately 10 oersteds during said magnetization step, providing a first output from said first voltage reading, providing a second output from said second voltage reading, combining said first and second outputs to provide a third output indicative of the difference between said first and second outputs, plotting an analog of the ratio of said first and said third outputs on a chart for each position of said coil of steel strip material.

3. The method as claimed in claim 2, including the step of:

plotting on a chart a visual indication of said ratio for each portion of said coil of steel strip material to provide an indication of steel quality for each portion of said coil of strip material, determining the mean average of said ratio on said chart, removing those portions of the coil of said coil of steel strip material which deviate from said mean average, and piecing the remaining portion of said coil together to form a coil of steel strip material of substantially uniform overall steel quality.

4. The method as claimed in claim 3, including the step of:

piecing together those portions of the coil of steel strip material removed therefrom in accordance with similar characteristics to form other coils of steel strip material with substantially similar uniform overall steel quality.

5. A method of testing steel strip material, comprising the steps of:

applying a specific quantity of magnetizing flux to a predetermined area of the steel strip material as it is moved past a flux application position;

obtaining a first measurement of the magnetizing force induced due to the flux applied to said predetermined area;

obtaining a second measurement of the magnetizing force induced due to the flux applied to said predetermined area as a predetermined percentage of said first obtained measurement;

combining said first and second obtained measurements to obtain the difference therebetween to obtain a third measurement characteristic of said combined measurements; and comparing said one of said first and second measurements with said third measurement to obtain a ratio between said last-mentioned one measurement to said third measurement.

6. The method as claimed in claim 5, including the steps of:

recording said ratio for each position of said steel strip to provide a profile of said coil of steel strip material, removing portions of said steel strip material from said coil of strip material which deviate from the predominant overall ratio of said coil of steel strip material, piecing together portions of said removed portions which have a ratio related to each other so that other coils of steel strip material are provided with a substantially uniform overall ratio to provide other coils of steel strip material with the substantially uniform overall ratio, thereby providing other coils of uniform overall quality.

7. The method as claimed in claim 5, including the steps of providing a visual representation of said first measurement and said third measurement on a strip chart recorder to provide a visual indication of the beginning of the change in quality from the overall quality just prior to the change in quality of the strip steel.

8. Continuous testing apparatus for determining the magnetic characteristics of a strip of moving material comprising:

a flux inducing and pick-up device including means to induce a magnetization current into said strip of moving material and means to pick-up two quantities characteristic of the same flux induced into said strip of material to produce a voltage output for each said quantities with said voltage outputs differing from each other, means responsive to said voltage outputs to produce a third output voltage which is a ratio of the output voltage of one of said quantities divided by the difference between said first voltage output and said other of said first-mentioned output voltages, whereby the overall average ratio is indicative of overall quality of said material.

9. Apparatus as defined in claim 8, said means to pick-up said two quantities including:

first and second flux pick-up coils adapted to pick-up flux induced into said strip of moving material, each producing a different output voltage for the same quantity of flux sensed;

said first pick-up coil producing a voltage greater than the voltage of said second pick-up coil; and, said responsive means including:

first and second circuits, said first circuit being coupled with said first pick-up coil and including means to produce a rectified voltage whose magnitude is characteristic of the voltage induced in said first flux pick-up coil, said second circuit being coupled with said first and said second pick-up coils and including means to produce a rectified voltage whose magnitude is characteristic of said voltage induced in said first flux pick-up coil and the voltage induced in said second flux pick-up coil, and divider means coupled to said first and second circuits to produce an output voltage derived from dividing said voltage output from said first circuit by the voltage output from said second circuit.

10. Apparatus as defined in claim 9, said first circuit including:

a first full wave diode bridge connected with said first pick-up coil, and a first digital D.C. voltmeter coupled with the output of said diode bridge to produce an analog output voltage of the voltage induced in said first pick-up coil;

said second circuit including:

a second full wave diode bridge connected with said second pick-up coil and the output of said first diode bridge to produce a rectified voltage output which is the difference between the voltages induced in said first and said second pick-up coils, and a second D.C. digital voltmeter coupled with said second diode bridge to produce an analog output voltage of said rectified voltage output.

11. Apparatus as defined in claim 10, said response means including:

a divider coupled with said first and second circuits, said divider being coupled with said first digital voltmeter to apply the output thereof as a numerator and being coupled with said second digital voltmeter to apply the output thereof as a denominator, thereby producing an output voltage characteristic of the dividend voltage of said first and said second circuits.

12. Apparatus as defined in claim 11, including:

a recorder to provide a chart display of the voltage output from said divider in accordance with the position of said strip of material being passed through said flux inducing and pick-up coils, said recorder including a first input responsive to the line speed of said strip material, and a second input coupled to the output of said divider, whereby to produce a direct reading chart indicating the magnitude of said voltage output from said divider for each position of said strip material as it passes said flux inducing and pick-up coils.

13. Apparatus as defined in claim 8, said flux inducing and pick-up device comprising:
   a magnetization coil for inducing a magnetic flux into said strip of moving material,
   a first flux pick-up coil associated with said magnetization coil responsive to the flux induced into said strip of moving material, said first coil having a first characteristic to produce a first output voltage characteristic of the magnetic quality of said material passing past said first pick-up coil,
   a second flux pick-up coil associated with said magnetization coil and said first flux pick-up coil responsive to the flux induced into said strip of moving material, said second coil having a second characteristic different from said first characteristic of said first coil for producing an output in accordance with said second characteristic and the characteristic of the magnetic material in response to the flux induced therein by said magnetization coil, said second coil producing a second output voltage which is different from said first output voltage.

14. Apparatus as defined in claim 13, said first coil having a greater number of turns than said second coil, whereby said first output voltage is of a greater magnitude than said second output voltage.

15. Apparatus as defined in claim 14, said responsive means including:
   first circuit means coupled with said first pick-up coil to produce an analog voltage characteristic of the magnitude of said first output voltage,
   said circuit means coupled with said second pick-up coil and said first circuit to produce an analog voltage characteristic of the magnitude of difference voltage between said first and second voltages, and
   divider means coupled to the outputs of said first and said second circuits to produce a voltage which is a ratio of said first output voltage and said difference voltage.

16. Apparatus as defined in claim 15, including a recorder to produce an output characteristic of said ratio voltage plotted against the position of the strip as it passes said flux inducing and pick-up device.

17. Apparatus as defined in claim 16, said recorder having chart including an abscissa illustrating the position of the strip material and an ordinate indicative of said ratio voltage, whereby to provide a visual indication of changes in said ratio voltage thereby indicating changes in the characteristic of the strip material as the recordation on said chart deviates from a substantially flat response.

18. Apparatus as claimed in claim 13, said responsive means including first and second circuit means, said first circuit means including first rectification means coupled with said first coil to produce a first rectified voltage output having a magnitude characteristic of the flux picked up by said first coil, and a first analog digital display device coupled to the output of said first rectifier means to produce an analog output voltage of the voltage induced into said first coil as the strip moves past said flux inducing and pick-up device; and said second circuit means including second rectification means and a second analog digital device, said second rectification means including first and second inputs and a single output, said first input being coupled to the output of said second coil, and said second input being coupled to the output of said first rectifier means, the input of said second digital display means being coupled to the output of said second rectification means, said second analog digital display device producing a second analog voltage output of the difference between the voltages induced into said first and said second coils.

19. Continuous testing apparatus for determining the magnetic characteristics of a moving workpiece which comprises a magnetization coil providing a magnetization force for introducing magnetic flux into said workpiece; a first pick-up coil associated with said magnetization coil responsive to the flux induced into said workpiece for producing an output voltage in accordance with the flux induced into said workpiece; and a second pick-up coil associated with said magnetization coil responsive to the flux induced into said workpiece, said second pick-up coil having a relatively greater number of turns displaced longitudinally from the longitudinal central portion of said magnetization coil than said first pick-up coil so as to produce an output voltage in accordance with the flux induced into said workpiece which is less than the output voltage of said first pick-up coil, said coils being arranged in coaxial relationship with said axis being substantially parallel to the direction of movement of the workpiece and means for obtaining a ratio from the pick-up coil voltages indicative of the quality of the workpiece.

20. Apparatus according to claim 19 in which said coils surround said workpiece, said magnetization coil and said first pick-up coil have substantially the same length and extend over substantially the same longitudinal distance with respect to said workpiece, and said second pick-up coil is of greater length than said first pick-up coil and extends longitudinally beyond each end thereof.

21. Apparatus according to claim 19 in which said coils surround said workpiece and have substantially the same length and extend over substantially the same longitudinal distance with respect to said workpiece and said pick-up coil having a greater number of turns adjacent each longitudinal end thereof than said first pick-up coil.

22. A method of obtaining a profile indicating quality of a continuous steel strip which comprises: moving said strip longitudinally; sequentially magnetizing sequential portions of said continuous strip to a controlled level of magnetization; sequentially providing a first output voltage signal indicative of the flux induced into said portions of said moving strip; sequentially providing a second output voltage signal indicative of the flux induced into said portions of said moving strip; said first and second output voltage signals being provided by flux induced from generally the same portion of the strip but with a greater proportion of the second voltage being obtained from areas longitudinally remote from the transverse center of said portion of the strip than the first voltage signal, said magnetization and said output voltages being obtained from coils arranged in co-axial relationship with said axis being substantially parallel to the direction of movement of said strip, and obtaining a ratio from said output voltage signals indicative of the quality of the strip.

23. The method of claim 22 including the step of comparing said voltage outputs to provide a continuous reading indicative of the quality of said strip throughout its length.

* * * * *